United States Patent [19]
O'Lenick, Jr.

[11] Patent Number: 5,298,656
[45] Date of Patent: Mar. 29, 1994

[54] ESTER QUATERNARY COMPOUNDS

[76] Inventor: Anthony J. O'Lenick, Jr., 743 Ridgeview Dr., Lilburn, Ga. 30247

[21] Appl. No.: 901,200

[22] Filed: Jun. 19, 1992

Related U.S. Application Data

[63] Continuation-in-part of Ser. No. 813,449, Dec. 26, 1991, Pat. No. 5,153,294.

[51] Int. Cl.$^5$ .................... C07C 209/00; C09F 5/00
[52] U.S. Cl. .................... 554/224; 554/52; 548/313.7
[58] Field of Search .................... 548/313.7; 564/224; 554/52

[56] References Cited

U.S. PATENT DOCUMENTS

| | | | |
|---|---|---|---|
| 3,445,440 | 5/1969 | Susi et al. | 260/89.5 |
| 3,517,045 | 6/1970 | Susi et al. | 260/459 |
| 4,144,122 | 3/1979 | Enanuelson et al. | 162/158 |
| 4,215,064 | 7/1980 | Lindenann et al. | 260/403 |
| 4,283,542 | 10/1981 | O'Lenick et al. | 548/112 |
| 4,675,359 | 6/1987 | Kadono | 554/52 |
| 4,764,306 | 8/1988 | Login | 554/52 |
| 4,781,863 | 11/1988 | Griffith | 554/52 |
| 4,800,077 | 1/1989 | O'Lenick et al. | 724/70 |
| 5,182,407 | 1/1993 | Sebag | 554/52 |
| 5,204,375 | 4/1993 | Kusakawa et al. | 554/52 |
| 5,221,794 | 6/1993 | Ackermain | 554/52 |

*Primary Examiner*—David B. Springer

[57] ABSTRACT

The present invention relates to a series of novel quaternary polymers and an intermediate useful in it's preparation. The compounds of the present invention are prepared by the reaction of chloracetic acid with a pendant hydroxyl group which is present on a polyoxyalkylene polymer, followed by the reaction of the halo-ester with a tertiary amine to give a quaternary compound. In a preferred embodiment the polyoxyalkylene glycol has been prepared by the reaction of both ethylene oxide and propylene oxide. In a more preferred embodiment, the ethylene oxide is at the terminal portion of the molecule and the propylene oxide is in the center.

13 Claims, No Drawings

ESTER QUATERNARY COMPOUNDS

RELATED APPLICATION

This application is a continuation in part of copending application Ser. No. 813,2449 filed Dec. 26, 1991, now U.S. Pat. No. 5,153,294.

BACKGROUND OF THE INVENTION

(1) Field of Invention

The present invention relates to a series of novel quaternary polymers and an intermediate useful in it's preparation. The polymers by virtue of the presence of a mixed polyoxyethylene/polyoxypropylene glycol in correct location within in the molecule, results in liquidity, low foam, solubility and enhanced reactivity as well as inverse cloud point. The correct selection of the proper molecule results in the optimum combination of desired properties.

Since the compounds of the present invention are high molecular weight, they have a high degree of oxidative stability, even at elevated temperatures. In addition, these compounds are non volatile and unlike many other traditional fatty quaternary compounds are non yellowing when applied to textile substrates and are non irritating to eyes and skin.

The compounds of the present invention are prepared by the reaction of chloracetic acid with a pendant hydroxyl group which is present on a polyoxyalkylene polymer, followed by the reaction of the halo-ester with a tertiary amine to give a quaternary compound. In a preferred embodiment the polyoxyalkylene glycol has been prepared by the reaction of both ethylene oxide and propylene oxide. In a more preferred embodiment, the ethylene oxide is at the terminal portion of the molecule and the propylene oxide is in the center. This results in the best combination of solubility and highest percentage reacted.

(2) Object of the Invention

It is the object of the present invention to provide a series of novel polymeric quaternary compounds which are nonfoaming or defoaming while providing lubricating and antistatic when applied to textiles and paper. The compounds of the present invention contain a nitrogen portion which is derived from a fatty tertiary amine. Incorporation of this type of group into the molecule results in increased solubility in many organic solvents. The compounds also contain varying amounts of ethylene oxide and propylene oxide in the molecule. This results in the ability to vary water solubility, foaming tendencies and introduce an inverse cloud point into the molecule.

Still another object of the present invention is to provide a series of quaternary polymers which have differing solubilities in water and organic solvents. This is achieved by selection of the raw materials chosen.

Application of the compounds of the invention can be from solvent, aqueous dispersion or solution, or applied neat in these process. It is anticipated that the effective conditioning concentration of the compound of this invention ranges from 0.1% to 25% by weight.

The polyoxyalkylene glycol polymers, suitable as raw materials, in a preferred embodiment, contain varying amounts of ethylene oxide, propylene oxide or mixtures thereof. The presence of a mixed polyoxyethylene/polyoxypropylene glycol in correct location within in the molecule, results in liquidity, low foam, solubility and enhanced reactivity. It also results in compounds with an inverse cloud point. Inverse cloud point phenomenon are well known to those skilled in the art of nonionic surface active agents. The inverse cloud point is defined as a temperature above which the polymer has minimal solubility in water. If heat is applied to an aqueous solution of the nonionic at the inverse cloud point the material will become insoluble, and the solution will turn milky. It is at this point that the polymer has minimal water solubility. Since the product is no longer in solution at above this temperature, it is within this temperature range that the product has maximum substantially to a fiber. The ability to use temperature to deposit a lubricant, antistat onto a fiber offers a great advantage in cost effectivness of fiber treatment, and results in less product usage.

(3) Description of the Arts and Practices

Standard fatty quaternary compounds are prepared by quaternization of a tertiary amine with such agents as benzyl chloride or di-methyl sulfate or di-ethyl sulfate or methyl chloride. These materials are relatively inexpensive but offer several key disadvantages. These include yellowing of fabrics, a tendency to build-up upon repeated treatment, and variability in hand (i.e. softness and feel). Standard softeners used are selected from the following classes:

Class #1. Alkyl Imidazoline Quaternary Compounds made from the quaternization of an imidazoline made by reacting diethylenetriamine, and a high molecular weight fatty acid such as stearic acid. The standard quaternizating agents are di-ethyl sulfate, or methyl chloride, or di-methyl sulfate, or methyl chloride or benzyl chloride.

Class #2. Alkyl or dialkyl tertiary amines quaternized with benzyl chloride or di-ethyl sulfate or methyl chloride or di-methyl sulfate.

Class #3. Quaternary compounds of ethoxylated, propoxylated or nonalkoxylated amido amines derived from the reaction of a high molecular weight fatty acid like stearic acid and a polyamine like diethylene triamine. The standard quaternizating agents are di-ethyl sulfate or di-methyl sulfate or methyl chloride or benzyl chloride.

Class #4. Amido amine salts derived from partially acid neutralized amines.

It is known that under certain catalytic conditions, epichlorohydrin reacts with certain alcohols to give an intermediate which can be used to react with tertiary amines to quaternary compounds. U.S. Pat. No. 3,445,440 to Susi (May 1969) and U.S. Pat. No. 3,517,045 to Susi (June 1970) teaches the use of chlorohydroxypropyl ether to alkylate specific tertiary amines which are the reaction product of a primary fatty amine and ethylene or propylene oxide. The compounds are used as antistatic agents in polymeric compositions such as polyolefin. The antistatic properties of these compounds are achieved by the minimization of static charges on the polymer surface. These anti-static materials are incorporated into the polymer melt and are effective by virtue of their insolubility in the molten polymer. The quaternary compounds migrate to the polymer surface and are effective antistatic agents.

U.S. Pat. No. 4,144,122 to Emanuelsson issued Mar. 13, 1979 teaches that tallow alcohol and certain other higher molecular weight alcohols and their alkoxylates can be reacted with epichlorohydrin, then subsequently with tertiary amines to give compounds suitable for paper debonding.

U.S. Pat. No. 4,215,064 to Lindeman et al issued Jul. 29, 1980 teaches that phosphobetaines can be prepared by the reaction of a phosphate or phosphite salt with epichlorohydrin under aqueous conditions. U.S. Pat. No. 4,283,541 to O'Lenick, et al, issued Aug. 11, 1981 teaches the process for the preparation of the phosphobetaines described in Lindemann (U.S. Pat. No. 4,215,064). None of these patents teach the compounds of the present invention.

U.S. Pat. No. 4,800,077 issued January 1989 to O'Lenick teaches guerbet alcohol quaternary compounds can be prepared by reacting epichlorohydrin with guerbet alcohols then subsequently reacting the intermediate with amines.

None of the above incorporate the ester functionality together with the polyoxyethylene/polyoxypropylene glycol into the quaternary compound. Consequently, the unique liquidity, low foam, solubility and enhanced reactivity as well as inverse cloud point are achieved. Additionally, epichlorohydrin is a highly reactive, toxic material even at very low levels. It is difficult to remove from aqueous surfactants. The compounds of this invention are epichlorohydrin free, and consequently do not have the inherent problems with toxicicty.

THE INVENTION $$R^6\overset{O}{\overset{\|}{C}}NH(CH_2)_3\overset{R^7}{\underset{R^8}{\overset{|}{N}}} \quad (II)$$

$R^6$ is alkyl having from 6 to 20 carbon atoms;
$R^7$ and $R^8$ are independently selected from the group consisting of methyl and ethyl; and $$\begin{array}{c}(CH_2)_2-N\\ |\quad\quad\quad\|\\ N\text{------}C-R^9\\ |\\ CH_2CH_2OH\end{array} \quad (III)$$

wherein $R^9$ is alkyl having from 6 to 20 carbon atoms.

The products of the present invention are prepared by reaction of a polyoxyalkylene glycol with a halo acid, most commonly chloracetic acid resulting in a halo ester which in a subsequent step is reacted with an amine to give the desired quaternary compounds.

The intermediate polyoxyalkylene glycol halo-ester is an additional aspect of the present invention. It is useful as an intermediate in the preparation of the compounds of the present invention.

$$H-O+CH_2-CH_2-O]_a+CH_2-CH(CH_3)-O]_b+CH_2-CH_2-O]_c[-CH_2-CH(CH_3)-O]_d-H +$$

$$Cl-CH_2-C(O)-OH \longrightarrow H_2O \uparrow \text{ and}$$

$$R^1-O+CH_2-CH_2-O]_a+CH_2-CH(CH_3)-O]_b+CH_2-CH_2-O]_c[-CH_2-CH(CH_3)-O]_d-R^1$$

wherein $R^1$ is $-C(O)-CH_2-Cl$

1) Summary of the Invention

The present invention relates to a series of novel quaternary polyoxyalkylene based polymers. These polymers have a polyoxyalkylene functional group present in the center of the molecule. The polymers by virtue of the presence of a mixed polyoxyethylene/polyoxypropylene glycol in correct location within in the molecule, results in liquidity, low foam, solubility and enhanced reactivity. It also results in compounds with an inverse cloud point.

The compounds of this invention are quaternary compounds prepared by the reaction of a polyoxyalkylene glycol polymer conforming to the following structure:

$$R^1-O-[-CH_2-CH_2O]_a-[-CH_2-CH(CH_3)-O]_b-[-CH_2-CH_2-O-]_c[-CH_2-CH(CH_3)-O]_d-R^1$$

wherein
$R^1$ is $-C(O)-CH_2-Cl$
a, b c and d are independently integers from 0 to 100, with the proviso that a+b+c+d be greater than 2, with tertiary amines conforming to the following structure;

$$\begin{array}{c}R^3\\ |\\ N-R^4\\ |\\ R^5\end{array} \quad (I)$$

$R^3$, $R^4$, and $R^5$ are each independently alkyl having from 1 to 20 carbon atoms;

wherein $R^1$ is $-C(O)-CH_2-Cl$

The compounds of the related invention of which this is a continuation in part are based upon the reaction of chloroacetic acid with a dimethicone copolyol. We have surprisingly found that the esterification reaction of the polyoxyalkylene glycol with the chloracetic acid and subsequent reaction with a tertiary amine results in a non-silicone based analog which has unexpected properties when compared to standard quats.

This approach also allows for the production of the desired quat, without undesired toxic byproducts. For example, we have attempted to prepare the following product;

$$Br-[-CH_2-CH_2-O]_a-[-CH_2-CH(CH_3)-O]_b-[-CH_2-CH_2-O]_c[-CH_2-CH(CH_3)-O]_d-Br$$

This was undertaken by the reaction of $PBr_3$ with the polyoxyalkylene glycol. While the bromide was prepared, the aggressive nature of the brominating agent surprisingly resulted in intolerable formation of toxic dioxane and crown ethers and destruction of the desired quat.

$$\begin{array}{cc}\begin{array}{c}CH_2-CH_2\\ O\quad\quad\quad O\\ CH_2-CH_2\end{array} & \text{and} \quad \begin{array}{c}CH_2-CH-CH_3\\ O\quad\quad\quad\quad O\\ CH_2-CH-CH_3\end{array}\end{array}$$

These materials are known to be toxic at very low concentrations and consequently render this process unacceptable as a commercial process.

The use of thionyl chloride, $PCl_3$ and related materials was equally unsuccessful and was abandoned. It was only the use of this new reaction sequence that a product free of toxic byproducts was prepared. This lack of toxic byproducts is an unexpected result which gives the unexpected advantage of materials which can be used commercially.

The resulting product is a linear molecule with cationic fatty moieties at each end and a polyoxyalkylene glycol derived backbone in the middle. This structure gives surprising results as will be described later.

The compounds of the present invention conform to the following structure:

$$R^2-O-[-CH_2-CH_2-O]_a-[-CH_2-CH(CH_3)-O]_b-[-CH_2-CH_2-O]_c-[-CH_2-CH(CH_3)-O]_d-R^2$$

wherein
$R^2$ is $-C(O)-CH_2-R^{10}$
a, b c and d are independently integers from 0 to 100, with the proviso that a+b+c+d be greater than 2;
$R^{10}$ is selected from the group consisting of

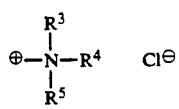 (I)

$R^3$, $R^4$, and $R^5$ are each independently alkyl having from 1 to 20 carbon atoms;

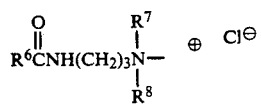

$R^6$ is alkyl having from 6 to 20 carbon atoms;
$R^7$ and $R^8$ are independently selected from the group consisting of methyl and ethyl; and

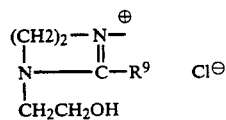 (III)

wherein $R^9$ is alkyl having from 6 to 20 carbon atoms.

RAW MATERIAL EXAMPLES

Polyoxyalkylene Glycol Compounds $$HO-[-CH_2-CH_2-O]_a-[-CH_2-CH(CH_3)-O]_b-[-CH_2-CH_2-O]_c-[-CH_2-CH(CH_3)-]_d-OH$$

wherein:
a, b c and d are independently integers from 0 to 100, with the proviso that a+b+c+d be greater than 2.

Class 1

Polyoxyethylene Glycols (b,c, and d are all 0.)

The following examples are presented with the values of a and as determined by analysis. Since products covered by trade name can change, the structure rather than the trade name is considered more important as an example.

| Example | Trade Name | Molecular Weight | a |
|---------|------------|------------------|-----|
| 1 | Phenoxide E-400 | 200 | 4 |
| 2 | Phenoxide E-300 | 300 | 6 |
| 3 | Phenoxide E-400 | 400 | 8 |
| 4 | Phenoxide E-600 | 600 | 12 |
| 5 | Phenoxide E-900 | 900 | 20 |
| 6 | Phenoxide E-1000 | 1,000 | 22 |
| 7 | Phenoxide E-1450 | 1,450 | 32 |
| 8 | Phenoxide E-3350 | 3,350 | 74 |
| 9 | Phenoxide E-4600 | 4,600 | 104 |
| 10 | Phenoxide E-8000 | 8,000 | 180 |

Phenoxide is a registered trademark of Phoenix Chemical Inc.

Class 2

$$HO-[-CH_2-CH_2-O]_a-[-CH_2-CH(CH_3)-O]_b-[-CH_2-CH_2-O]_c-[-CH_2-CH(CH_3)-O]_d-H$$

The following examples are presented with the values of a, b and c as determined by analysis. Since products covered by trade name can change, the structure, rather than the trade name is considered more important as an example.

| Example | Trade Name | a | b | c |
|---------|------------|-----|------|-----|
| 11 | Phoenix L-31 | 1.0 | 2.1 | 1.0 |
| 12 | Phoenix L-35 | 5.0 | 10.0 | 5.0 |
| 13 | Phoenix L-42 | 2.5 | 5.0 | 2.5 |
| 14 | Phoenix L-43 | 3.0 | 8.0 | 3.0 |
| 15 | Phoenix L-44 | 6.0 | 11.0 | 6.0 |
| 16 | Phoenix L-61 | 2.0 | 4.0 | 2.0 |
| 17 | Phoenix L-62 | 4.0 | 8.0 | 4.0 |
| 18 | Phoenix L-63 | 6.0 | 12.0 | 6.0 |
| 19 | Phoenix L-64 | 8.0 | 16.0 | 8.0 |
| 20 | Phoenix L-72 | 5.0 | 9.5 | 5.0 |
| 21 | Phoenix L-81 | 3.0 | 5.0 | 3.0 |
| 22 | Phoenix L-92 | 6.0 | 12.5 | 6.0 |
| 23 | Phoenix L-101 | 4.0 | 7.5 | 4.0 |
| 24 | Phoenix L-121 | 4.5 | 9.0 | 4.5 |
| 25 | Phoenix L-122 | 9.0 | 18.0 | 9.0 |

Phoenix is a registered trademark of Phoenix Chemical

Class 3

Polyoxypropylene Compounds (a, c and d are each 0)

$$HO-[-CH_2-CH_2-O]_a-[-CH_2-CH(CH_3)-O]_b-[-CH_2-CH_2-O]_c-[-CH_2-CH(CH_3)-O]_d-H$$

a, c and d are all zero.

| Example | Trade Name | Molecular Weight | b |
|---------|------------|------------------|-----|
| 26 | Alkapol PPG 425 | 425 | 7 |
| 27 | Alkapol PPG 600 | 600 | 10 |
| 28 | Alkapol PPG 1000 | 1000 | 17 |

Alkapol is a registered trade mark of Alkaril Chemicals Inc. Winder Ga.

Class 4

$$HO-[-CH_2-CH_2-O]_a-[-CH_2-CH(CH_3)-O]_b-[-CH_2-CH_2-O]_c-[-CH_2-CH(CH_3)-O]_d-H$$

The following examples are presented with the values of b, c and d as determined by analysis.

| Example | Trade Name | b | c | d |
|---|---|---|---|---|
| 29 | Phoenix R 4 | 1.0 | 2.1 | 1.0 |
| 30 | Phoenix R 20 | 5.0 | 10.0 | 5.0 |
| 31 | Phoenix R 10 | 2.5 | 5.0 | 2.5 |
| 32 | Phoenix R 16 | 4.0 | 8.0 | 4.0 |
| 33 | Phoenix R 22 | 6.0 | 11.0 | 6.0 |
| 34 | Phoenix R 8 | 2.0 | 4.0 | 2.0 |
| 35 | Phoenix R 14 | 3.0 | 8.0 | 3.0 |
| 36 | Phoenix R 2 | 6.0 | 12.0 | 6.0 |
| 37 | Phoenix R 32 | 8.0 | 16.0 | 8.0 |
| 38 | Phoenix R 19 | 5.0 | 9.0 | 5.0 |
| 39 | Phoenix R 11 | 3.0 | 5.0 | 3.0 |
| 40 | Phoenix R 24 | 6.0 | 12.5 | 6.0 |
| 41 | Phoenix R 15 | 4.0 | 7.5 | 4.0 |
| 42 | Phoenix R 18 | 4.5 | 9.0 | 4.5 |
| 43 | Phoenix R 36 | 9.0 | 18.0 | 9.0 |
| 44 | Phoenix R 101 | 10.0 | 10.0 | 10.0 |

Preparation of the Polyoxyalkyleneglycol Halo Ester

Reaction Sequence

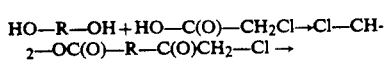
HO—R—OH + HO—C(O)—CH$_2$Cl → Cl—CH$_2$—OC(O)—R—C(O)CH$_2$—Cl →

R is the polyoxyalkylene moiety.

The following examples further illustrate the objects and advantages of this invention, though it should be understood that the various reactants and amounts thereof, reaction conditions, and other details are merely illustrative and should not be construed to unduly limit this invention.

General Procedure

Place the indicated amount of the polyoxyalkylene glycol shown in a suitable vessel is added the desired amount of catalyst as shown under good agitation and a nitrogen sparge. Then 95.0 grams of monochloracetic acid is added. A molar excess of 0.1 to 0.5 of chloroacetic acid is added. The temperature is held between 160–200 degrees C. for two to six hours. Reaction progress is monitored by acid value analysis and at the end of the reaction reaches theoretical for the mole ratio used.

| Example | Example Number | Grams |
|---|---|---|
| 45 | 1 | 100 |
| 46 | 2 | 150 |
| 47 | 3 | 200 |
| 48 | 4 | 300 |
| 49 | 5 | 450 |
| 50 | 6 | 500 |
| 51 | 7 | 725 |
| 52 | 8 | 1,675 |
| 53 | 9 | 2,300 |
| 54 | 10 | 4,000 |
| 55 | 5 | 900 |
| 56 | 11 | 106 |
| 57 | 12 | 515 |
| 58 | 13 | 258 |
| 59 | 14 | 368 |
| 60 | 15 | 589 |
| 61 | 16 | 206 |
| 62 | 17 | 412 |
| 63 | 18 | 618 |
| 64 | 19 | 824 |
| 65 | 20 | 501 |
| 66 | 21 | 280 |
| 67 | 22 | 632 |
| 68 | 23 | 441 |
| 69 | 24 | 463 |
| 70 | 25 | 927 |
| 71 | 26 | 213 |
| 72 | 27 | 300 |
| 73 | 28 | 500 |
| 74 | 29 | 105 |
| 75 | 30 | 515 |
| 76 | 31 | 258 |
| 77 | 32 | 412 |
| 78 | 33 | 596 |
| 79 | 34 | 206 |
| 80 | 35 | 353 |
| 81 | 36 | 618 |
| 82 | 37 | 824 |
| 83 | 38 | 493 |
| 84 | 39 | 287 |
| 85 | 40 | 629 |
| 86 | 41 | 401 |
| 87 | 42 | 463 |
| 88 | 43 | 927 |

Quaternary Reaction Sequence

All amine reactants are commercially available from Tomah Products Division of Exxon Chemicals Milton Wis.

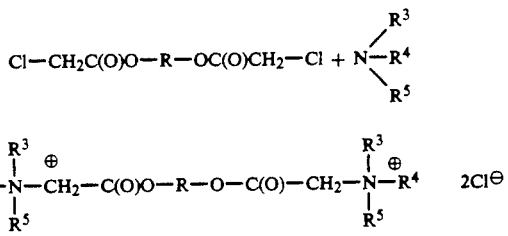

R contains the polyoxyalkylene portion of the molecule.

The following examples further illustrate the objects and advantages of this invention, though it should be understood that the various reactants and amounts thereof, reaction conditions, and other details are merely illustrative and should not be construed to unduly limit this invention.

Amine Reactant Group 1

The reactants are tertiary amines conforming to the following structure;

$$R^4-\underset{\underset{R^5}{|}}{\overset{\overset{R^3}{|}}{N}}-R^5$$

| Example Number | $R^3$ | $R^4$ | $R^5$ |
|---|---|---|---|
| 89 | $C_{10}H_{21}$ | $CH_3$ | $CH_3$ |
| 90 | $C_{12}H_{25}$ | $CH_3$ | $CH_3$ |
| 91 | $C_{14}H_{29}$ | $CH_3$ | $CH_3$ |
| 92 | $C_{16}H_{33}$ | $CH_3$ | $CH_3$ |
| 93 | $C_{18}H_{37}$ | $CH_3$ | $CH_3$ |
| 94 | $C_{20}H_{41}$ | $CH_3$ | $CH_3$ |
| 95 | $C_{10}H_{21}$ | $C_{16}H_{33}$ | $CH_3$ |
| 96 | $C_{12}H_{25}$ | $C_{18}H_{37}$ | $CH_3$ |
| 97 | $C_{14}H_{29}$ | $C_{20}H_{41}$ | $CH_3$ |
| 98 | $C_{16}H_{33}$ | $C_{10}H_{21}$ | $CH_3$ |
| 99 | $C_{18}H_{37}$ | $C_{12}H_{25}$ | $CH_3$ |
| 100 | $C_{20}H_{41}$ | $C_{14}H_{29}$ | $CH_3$ |
| 101 | $C_6H_{13}$ | $C_6H_{13}$ | $C_6H_{13}$ |
| 102 | $C_2H_5$ | $CH_3$ | $C_2H_5$ |

-continued

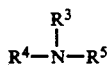

| Example Number | $R^3$ | $R^4$ | $R^5$ |
|---|---|---|---|
| 103 | $C_{10}H_{21}$ | $C_{10}H_{21}$ | $C_{10}H_{21}$ |

Amine Reactant Group 2

The reactants are amido tertiary amines conforming to the following structure;

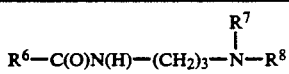

| Example Number | $R^6$ | $R^7$ | $R^8$ |
|---|---|---|---|
| 104 | $C_5H_{11}$ | $CH_3$ | $CH_3$ |
| 105 | $C_7H_{15}$ | $CH_3$ | $CH_3$ |
| 106 | $C_9H_{19}$ | $CH_3$ | $CH_3$ |
| 107 | $C_{11}H_{23}$ | $CH_3$ | $CH_3$ |
| 108 | $C_{13}H_{27}$ | $CH_3$ | $CH_3$ |
| 109 | $C_{15}H_{31}$ | $CH_3$ | $CH_3$ |
| 110 | $C_{17}H_{35}$ | $CH_3$ | $CH_3$ |
| 111 | $C_{19}H_{39}$ | $CH_3$ | $CH_3$ |
| 112 | $C_{19}H_{39}$ | $CH_2CH_3$ | $CH_2CH_3$ |
| 113 | $C_{11}H_{23}$ | $CH_2CH_3$ | $CH_2CH_3$ |
| 114 | $C_5H_{11}$ | $CH_2CH_3$ | $CH_2CH_3$ |
| 115 | $C_5H_{11}$ | $CH_3$ | $CH_3$ |
| 116 | $C_7H_{15}$ | $CH_3$ | $CH_3$ |
| 117 | $C_9H_{19}$ | $CH_3$ | $CH_3$ |
| 118 | $C_{11}H_{23}$ | $CH_3$ | $CH_3$ |
| 119 | $C_{13}H_{27}$ | $CH_3$ | $CH_3$ |
| 120 | $C_{15}H_{31}$ | $CH_3$ | $CH_3$ |
| 121 | $C_{17}H_{35}$ | $CH_3$ | $CH_3$ |
| 122 | $C_{19}H_{39}$ | $CH_3$ | $CH_3$ |

Amine Reactant Group 3

The reactants are imidazoline compounds conforming to the following structure;

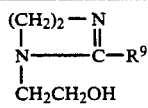

| Example Number | $R^9$ |
|---|---|
| 123 | $C_5H_{11}$ |
| 124 | $C_7H_{15}$ |
| 125 | $C_9H_{19}$ |
| 126 | $C_{11}H_{23}$ |
| 127 | $C_{13}H_{27}$ |
| 128 | $C_{15}H_{31}$ |
| 129 | $C_{17}H_{35}$ |
| 130 | $C_{19}H_{39}$ |

General Reaction Procedure

The products of the present invention are generally prepared in aqueous solution or dispersion. The preferred concentration is about 50% solids. Additionally, alcohols such as methanol, ethanol, isopropanol, glycols such as ethylene glycol, propylene glycol, polyoxypropylene glycol, polyoxyethylene glycol, hexylene glycol, and cyclomethicone can be added to improve clarity if desired.

To a suitable flask, equipped with a thermometer and agitator is added the specified amount of water. Heat to 50° C. Next add the specified amount of the type of amine reactant and the specified amount of the specified amine under good agitation. The reaction mass is heated to 85°–95° C. and held from between 5 and 15 hours. The reaction progress is monitored by % inorganic chloride, which approaches 98% of theoretical.

EXAMPLE 131

To a suitable flask, equipped with a thermometer and agitator is added 250.0 of water. Heat to 50° C. Next add 92.5 grams of amine reactant (Example 89). Next add the specified amount of the specified halo intermediate (example 45) under good agitation. The reaction mass is heated to 85°–95° C. and held from between 5 and 10 hours. The reaction progress is monitored by % inorganic chloride, which approaches 98% of theoretical.

EXAMPLES 132–175

Example 131 is repeated, only this time the specified amount of water is substituted. The type and amount of halo reactant and amine are also substituted.

| | Amine Reactants | | Halo Glycol Reactant | | Water |
|---|---|---|---|---|---|
| Example | Example | Grams | Example | Grams | Grams |
| 132 | 90 | 100.5 | 46 | 188.0 | 300.0 |
| 133 | 91 | 113.5 | 47 | 238.0 | 400.0 |
| 134 | 92 | 126.5 | 48 | 338.0 | 500.0 |
| 135 | 93 | 139.5 | 49 | 488.0 | 700.0 |
| 136 | 94 | 152.5 | 50 | 538.0 | 700.0 |
| 137 | 95 | 182.0 | 51 | 763.0 | 900.0 |
| 138 | 96 | 203.0 | 52 | 1688.0 | 2000.0 |
| 139 | 97 | 229.0 | 53 | 2338.0 | 2700.0 |
| 140 | 98 | 182.0 | 54 | 4038.0 | 4500.0 |
| 141 | 99 | 203.0 | 56 | 91.0 | 400.0 |
| 142 | 100 | 229.0 | 57 | 295.5 | 650.0 |
| 143 | 101 | 125.5 | 58 | 166.8 | 350.0 |
| 144 | 102 | 35.0 | 59 | 222.0 | 500.0 |
| 145 | 103 | 218.5 | 60 | 332.2 | 600.0 |
| 146 | 104 | 99.5 | 61 | 141.0 | 250.0 |
| 147 | 105 | 113.5 | 62 | 244.0 | 450.0 |
| 148 | 106 | 127.5 | 63 | 347.0 | 500.0 |
| 149 | 107 | 141.5 | 64 | 450.0 | 700.0 |
| 150 | 108 | 155.5 | 65 | 288.1 | 500.0 |
| 151 | 109 | 169.5 | 66 | 177.8 | 350.0 |
| 152 | 110 | 183.5 | 67 | 354.4 | 600.0 |
| 153 | 111 | 197.5 | 68 | 258.6 | 500.0 |
| 154 | 112 | 168.5 | 69 | 269.8 | 500.0 |
| 155 | 113 | 155.5 | 70 | 501.5 | 700.0 |
| 156 | 114 | 113.5 | 71 | 181.0 | 400.0 |
| 157 | 115 | 320.0 | 72 | 226.0 | 550.0 |
| 158 | 116 | 2464.0 | 73 | 301.0 | 3500.0 |
| 159 | 117 | 150.0 | 74 | 90.6 | 300.0 |
| 160 | 118 | 164.0 | 75 | 295.5 | 500.0 |
| 161 | 119 | 891.0 | 76 | 166.8 | 750.0 |
| 162 | 120 | 685.0 | 77 | 244.0 | 1000.0 |
| 163 | 121 | 551.5 | 78 | 336.0 | 1000.0 |
| 164 | 122 | 565.5 | 79 | 141.0 | 900.0 |
| 165 | 123 | 92.0 | 80 | 214.5 | 350.0 |
| 166 | 124 | 106.0 | 81 | 347.0 | 500.0 |
| 167 | 125 | 120.0 | 82 | 450.0 | 600.0 |
| 168 | 126 | 134.0 | 83 | 284.5 | 500.0 |
| 169 | 127 | 148.0 | 84 | 181.5 | 450.0 |
| 170 | 128 | 162.0 | 85 | 352.5 | 600.0 |
| 171 | 129 | 176.0 | 86 | 238.5 | 500.0 |
| 172 | 130 | 176.0 | 87 | 269.8 | 500.0 |
| 173 | 130 | 175.0 | 88 | 501.5 | 800.0 |
| 174 | 129 | 92.5 | 45 | 138.0 | 350.0 |
| 175 | 128 | 100.5 | 46 | 188.0 | 375.0 |

RESULTS

Each of the compounds exhibit different properties.

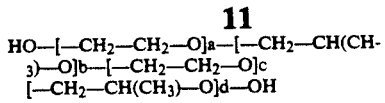

Class 1

Polyoxyethylene glycols (i.e. b, c, and d are 0.)

The terminal hydroxyl groups are on poyloxyethylene groups, making them primary. This results in a less sterically hindered hydroxyl group and higher conversions to the halo ester than those compounds based upon the secondary hydroxyl group. Conversions of over 99% are not uncommon. The polyoxyethylene group is hydrophyllic making the products based upon this group more water soluble and higher foamers compared to the other groups. These materials also tend to have the highest melting points compared to it's homologs in the other classes.

Class 2

Polyoxyethylene/Polyoxyoxypropylene/Polyoxyethylene glycol (i.e. a is zero)

The terminal hydroxyl groups are on poyloxyethylene groups, making them primary. This results in a less sterically hindered hydroxyl group and higher conversions to the halo ester than those compounds based upon the secondary hydroxyl group. Conversions of over 99% are not uncommon. The presence of the polyoxypropylene group in the center of the molecule introduces hydrophobic properties and surprisingly makes the products better fiber lubricants. The products are of intermediate water soluble, exhibit moderate foam, and provide good wetting properties compared to the homologs of other groups.

Class 3

Polyoxypropylene Compounds (a, c and d are each 0)

The terminal hydroxyl groups are on polyoxypropylene groups, making them secondary. This results in a more steric hindrance at hydroxyl group and lower conversions to the halo ester than those compounds based upon the primary hydroxyl group. Conversions of 93–95% are achieved with longer reaction times. The presence of just the polyoxypropylene group in the molecule makes the products very hydrophobic and surprisingly makes the products outstanding defoaming fiber lubricants. The products are water insoluble, destroy foam, and provide minimal wetting properties compared to the homologs of other groups.

Class 4

Polyoxypropylene/Polyoxyethylene/Polyoxypropylene glycol (i.e. d is zero)

The terminal hydroxyl groups are on polyoxypropylene groups, making them secondary. This results in a more steric hindrance and longer reaction times and somewhat lower conversions to the halo ester than those compounds based upon the primary hydroxyl group. The presence of the polyoxypropylene group in the terminal positions of the molecule introduces surprisingly liquidity, hydrophobicity, hydrolytic stability and lubrication properties when compared to the homologs of other groups.

Consequently, based upon unexpected properties, the products based upon group 4 are the most preferred, followed by the products based upon the group 2 glycols.

The products based upon the alkylamido amines are preferred due to the fact that they have the best fiber lubrication properties of any class.

The products based upon the heterocyclic amines are also preferred due to the fact that they have the best non-yellowing softening properties of any class.

What is claimed:

1. A quaternary compound which conforms to the following structure:

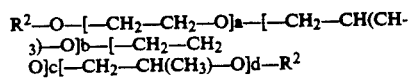

wherein:

$R^2$ is —C(O)—CH$_2$—R$^{10}$;

a, b c and d are independently integers from 0 to 100, with the proviso that a+b+c+d be greater than 2;

$R^{10}$ is

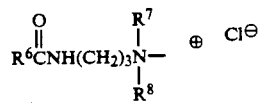

R6 is alkyl having from 6 to 20 carbon atoms;

R7 and R8 are independently selected from the group consisting of methyl and ethyl.

2. A compound of claim 1 wherein b, c and d are each zero.

3. A compound of claim 1 wherein only d is zero.

4. A compound of claim 1 wherein a, c and d are each zero.

5. A compound of claim 1 wherein only a is zero.

6. A compound of claim 1 wherein $R^7$ is CH$_3$ and $R^6$ is C$_5$H$_{11}$.

7. A compound of claim 1 wherein $R^7$ is CH$_3$ and $R^6$ is C$_7$H$_{15}$.

8. A compound of claim 1 wherein $R^7$ is CH$_3$ and $R^6$ is C$_9$H$_{19}$.

9. A compound of claim 1 wherein $R^7$ is CH$_3$ and $R^6$ is C$_{11}$H$_{23}$.

10. A compound of claim 1 wherein $R^7$ is CH$_3$ and $R^6$ is C$_{13}$H$_{27}$.

11. A compound of claim 1 wherein $R^7$ is CH$_3$ and $R^6$ is C$_{15}$H$_{31}$.

12. A compound of claim 1 wherein $R^7$ is CH$_3$ and $R^6$ is C$_{17}$H$_{35}$.

13. A compound of claim 1 wherein $R^7$ is CH$_3$ and $R^6$ is C$_{19}$H$_{39}$.

* * * * *